(12) United States Patent
Qian et al.

(10) Patent No.: US 11,008,357 B2
(45) Date of Patent: May 18, 2021

(54) METHOD FOR PREPARING CANAGLIFLOZIN AMORPHOUS FORM

(71) Applicants: Zhejiang Huahai Pharmaceutical Co., Ltd., Taizhou (CN); Zhejiang Huahai Zhicheng Pharmaceutical Co., Ltd., Taizhou (CN)

(72) Inventors: Gang Qian, Taizhou (CN); Yanbao Zhou, Taizhou (CN); Linxiang Zhang, Taizhou (CN); Wenling Zhang, Taizhou (CN)

(73) Assignees: ZHEJIANG HUAHAI PHARMACEUTICAL CO., LTD. (CN); ZHEJIANG HUAHAI ZHICHENG PHARMACEUTICAL CO., LTD. (CN)

(*) Notice: Subject to any disclaimer, the term of this patent is extended or adjusted under 35 U.S.C. 154(b) by 0 days.

(21) Appl. No.: 16/486,985

(22) PCT Filed: Feb. 6, 2018

(86) PCT No.: PCT/CN2018/075417
§ 371 (c)(1),
(2) Date: Aug. 19, 2019

(87) PCT Pub. No.: WO2018/149327
PCT Pub. Date: Aug. 23, 2018

(65) Prior Publication Data
US 2020/0165284 A1 May 28, 2020

(30) Foreign Application Priority Data
Feb. 20, 2017 (CN) .......................... 201710089871.9

(51) Int. Cl.
*C07H 7/06* (2006.01)

(52) U.S. Cl.
CPC ...................................... *C07H 7/06* (2013.01)

(58) Field of Classification Search
None
See application file for complete search history.

(56) References Cited

FOREIGN PATENT DOCUMENTS

| CN | 104119323 A | 10/2014 |
|---|---|---|
| CN | 104402946 A | 3/2015 |
| WO | 2014/195966 A2 | 12/2014 |
| WO | 2015/181692 A2 | 12/2015 |
| WO | 2016/098016 A1 | 6/2016 |

OTHER PUBLICATIONS

Giuletti (Sep. 19, 2012). Crystallization by Antisolvent Addition and Cooling, Crystallization—Science and Technology, Marcello Rubens Barsi Andreeta, IntechOpen. (Year: 2012).*
International Search Report for International Application No. PCT/CN2018/075417 dated May 3, 2018.

* cited by examiner

*Primary Examiner* — Layla D Berry
(74) *Attorney, Agent, or Firm* — Suiter Swantz pc llo

(57) ABSTRACT

Disclosed is a method for preparing a canagliflozin form. The method comprises the following steps: adding canagliflozin into an organic solvent and dissolving same, then distilling into a certain amount of an oil; then, adding an anti-solvent to the oil, stirring same with a precipitated solid, cooling, filtering, and drying to obtain the canagliflozin amorphous form. The preparation method has the characteristics of a low solvent ratio, a high yield, a simple operation, easy recovery, less three wastes and good producibility, with the resulting product having a stable quality, good fluidity, and being suitable for the preparation of formulations, etc., and the preparation process is easy to apply to large commercial production, and has a high value in terms of promotion and application.

18 Claims, 3 Drawing Sheets

METHOD FOR PREPARING CANAGLIFLOZIN AMORPHOUS FORM

The present application claims the priority of the Chinese Patent Application No. 201710089871.9, filed before the CNIPA on Feb. 20, 2017, entitled "METHOD FOR PREPARING CANAGLIFLOZIN AMORPHOUS FORM", which is hereby incorporated by reference in its entirety.

FIELD OF THE INVENTION

The present invention relates to the field of medical chemistry, in particular to a method for preparing a canagliflozin amorphous form.

BACKGROUND OF THE INVENTION

Canagliflozin, with the chemical name (1S)-1, 5-dehydro-1-C-[3-[[5-(4-fluorophenyl)-2-thienyl]methyl]-4-methylphenyl]-D-gluci tol, and the chemical structure thereof is shown as follows:

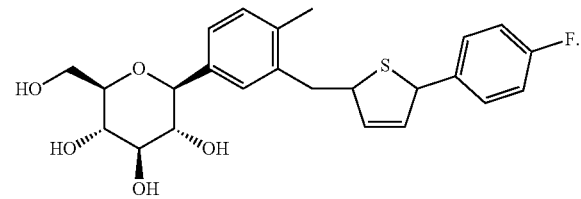 [SMILES: Cc1ccc([C@@H]2O[C@H](CO)[C@@H](O)[C@H](O)[C@H]2O)cc1CC1C=CC(c2ccc(F)cc2)S1]

Canagliflozin is a selective sodium-glucose co-transporter 2 (SGLT2) inhibitor developed by Johnson & Johnson in the United States. It is mainly used for the treatment of patients with type II diabetes, for which neither exercise nor diet control is ineffective. It came into the market of the US in March 2013 approved by FDA approval. This product allows lowering blood sugar by decomposing glucose and excreting it through the kidney. In addition to good glycemic control, the most striking effects of canagliflozin are weight loss and few hypoglycemia events. These effects result in a very broad prospect of canagliflozin.

In recent years, it is reported in the literatures that polymorphisms, which is a characteristic of some molecule and molecular complexes, exists in canagliflozin. Canagliflozin is a water-insoluble compound, thus research on its crystal form is of great significance.

The earliest report of a canagliflozin crystal form is patent WO2008069327A1 of Mitsubishi Pharmaceutical Co., Ltd., Japan, which reports a canagliflozin hemihydrate having characteristic diffraction at 2θ angles of about 4.36°, 13.54°, 16.00°, 19.32° and 20.80°±0.2° in its X-ray diffraction pattern. The water content of the TGA analysis of the hydrate crystal form is 1.7%. This crystal form is obtained by curing in a mixed solvent system of ethyl acetate/diethyl ether/water or acetone/water. At the same time, the patent also discloses a canagliflozin amorphous form, but the preparation method thereof is not disclosed.

Patent CN101801371 discloses another canagliflozin crystal form having characteristic diffraction at 2θ angles of 10.9°, 15.5°, 17.3°, 18.8° and 20.3°±0.2° in an X-ray powder diffraction pattern. This crystal form is obtained by crystallization in a mixed solvent system of ethyl acetate/n-heptane/water.

Patents CN103980261, CN103980262, and CN103936725 respectively disclose the canagliflozin crystal forms A, B, and C, and the respective preparation methods thereof, which are all prepared by using a mixed solvent system. Patent CN103889429 discloses a method for the preparation of a canagliflozin amorphous form, which is prepared by adding n-heptane to a heated solution of canagliflozin in toluene.

Patent CN104119323 discloses a method for preparing a canagliflozin amorphous form, which is prepared by adding a solution of a canagliflozin in benign solvent to a poor solvent for curing. Since the method is explosive crystallization, the resulting particles are relatively small, have static electricity, and are easy to coalesce.

Patent CN105541817A discloses a method for preparing a canagliflozin amorphous form, which is prepared by melting and curing via heat treatment.

Patent WO2014195966 discloses a method for preparing a canagliflozin amorphous form, which is prepared by dissolving canagliflozin in one or more organic solvents to form a solution, followed by spray drying or distillation.

Since the structural formula of canagliflozin comprises 1-β-D-glucopyranosyl group, canagliflozin has a property of being difficult to crystallize in a solution, and most of the crystal form preparation processes require the addition of seed crystals for inducing crystallization. At the same time, almost all the crystal preparation processes comprise a mixed solvent system with a large amount of solvent which is quite difficult to recovery, and brings a great negative impact on the environment.

SUMMARY OF THE INVENTION

An object of the present invention is to provide a method for preparing a canagliflozin amorphous form, which is simple, easy to recover the solvent, with high yield, low demand in equipment, and suitable for industrial production.

The invention is achieved by the following technical solutions: a method for preparing a canagliflozin amorphous form, comprising:
adding canagliflozin to an organic solvent to dissolve, distilling to obtain an oil, adding an anti-solvent to the oil, stirring to precipitate a solid, cooling, filtering, and drying to obtain a canagliflozin amorphous form.

In the preparation method provided by the present invention, the organic solvent is selected from the group consisting of ethyl acetate, toluene, ethanol, methanol, acetone, dichloromethane, tetrahydrofuran, methyl tert-butyl ether and isopropyl ether, preferably selected from ethyl acetate, ethanol and methyl tert-butyl ether.

In the preparation method provided by the present invention, a ratio of a mass of canagliflozin to a volume of the organic solvent is 1 g: (0.5-20) ml, preferably 1 g: (1-5) ml.

In the preparation method provided by the present invention, dissolving is performed at a temperature of −10° C. to 120° C., preferably 30° C. to 80° C.

In the preparation method provided by the present invention, a mass of the oil is 1.0-1.3 times, preferably 1.05-1.1 times of a mass of canagliflozin. If the residue of benign solvent in the oil is too much, the curing time of the product will be prolonged, even the product will not cure. If the residue of benign solvent in the oil is too little, industrial production will be difficult to achieve, the product will bond to the wall resulting in yield loss.

In the preparation method provided by the present invention, the anti-solvent is selected from the group consisting of n-hexane, cyclohexane and n-heptane; preferably cyclohexane or n-heptane.

In the preparation method provided by the present invention, a ratio of the mass of canagliflozin to the volume of the organic solvent is 1 g: (1-20) ml, preferably 1 g: (3-6) ml.

In the preparation method provided by the present invention, adding the anti-solvent or stirring is performed at a temperature of 0° C. to 50° C., preferably 10° C. to 30° C.

In the preparation method provided by the present invention, the solid is cooled to −20° C. to 20° C., preferably −10° C. to 10° C.

In the preparation method provided by the present invention, drying is performed at a temperature of 10° C. to 40° C., preferably 20° C. to 30° C.

The preferred technical solution of the method for preparing a canagliflozin amorphous form provided by the present invention is as follows:
adding canagliflozin to an organic solvent, heating to 30° C. to 80° C. to dissolve; after dissolving, distilling the canagliflozin solution at 30° C. to 80° C. to obtain an oil, controlling a mass of the oil to be 1.05 to 1.1 times of a mass of canagliflozin, adding an anti-solvent to the oil, stirring to precipitate a solid at 10° C. to 30° C., cooling to −10° C. to 10° C., filtering, and drying at 20° C. to 30° C. to obtain a canagliflozin amorphous form.

The X-ray powder diffraction pattern of the canagliflozin amorphous form obtained according to the present invention has the characteristics as shown in FIG. 1, where there is no crystallization peak and only one diffuse scattering peak at 10° to 30°. As shown in FIG. 2, DSC of the canagliflozin amorphous form shows an endothermic peak at 40° C. to 50° C., which peaks at 47° C. (endothermic peak).

The advantageous technical effects of the method for preparing a canagliflozin amorphous form provided by the present invention, compared with the prior art, include:
1. The preparation method of the present invention has less product loss and high yield as high as 95%;
2. The method provided by the present invention comprises no mixing of solvents, the solvents are easy to recover, resulting in less waste gas, waste water and industrial residue, and less environmental harm;
3. The method provided by the present invention has a small solvent ratio and low cost;
4. The preparation process of the present invention has a good reproducibility, a simple operation and is easy for large-scale commercial production;
5. The canagliflozin amorphous form obtained according to the method of the present invention has stable quality, good fluidity, and is suitable for the preparation of a formulation.

DESCRIPTION OF THE DRAWINGS

In order to illustrate the technical solution of the examples of the present invention and the prior art more clearly, the following description of the examples and the drawings used in the prior art will be briefly described. It is obvious to those skilled in the art that the accompanying drawings in the following description are only some examples of the present invention, and those skilled in the art can obtain other figures from these figures without any inventive efforts.

DETAILED DESCRIPTION OF THE INVENTION

In order to further understand the present invention, the preferred embodiments of the present invention are described in combination with the examples. However, it should be understood that the description is only intended to further illuminate the features and advantages of the present invention, and is not intended to limit the scope of the claims.

Starting Materials and General Test Methods:

The starting materials of canagliflozin (referred to as canagliflozin) used in the following examples was prepared in accordance with WO 2005012326.

X-ray powder diffraction (XRD) instrument: X'pert Pro type, PANalytical B.V., Netherlands: radiation source: copper target ($\alpha$=1.54060 Å), scanning at room temperature: voltage: 45 kv, current: 40 mA, starting 2θ: 2000°, scanning range: 3.000°-50.0000°, step size: 0.017°, measuring time: 50.2 seconds/step.

Differential Scanning calorimetry (DSC) instrument: DSC1 type, METTLER TOLEDO, Switzerland, range between 30° C. and 300° C., heating rate: 10° C./min, nitrogen flow rate: 40 ml/min.

Infrared spectrophotometry (FTIR) analytical instrument: Nicolet iS5 Fourier Transform Infrared Spectrometer, USA: potassium bromide pellet technique, resolution: 4.0 cm$^{-1}$.

Polarizing microscope: Olympus CX41, objective lens 4 times, eyepiece 10 times. The formula for calculating the yield: yield=(prepared mass of the canagliflozin amorphous form/mass of the canagliflozin starting material)×100%.

Example 1

20 g of canagliflozin and 60 ml of ethyl acetate were added to the reaction flask. The mixture was stirred at a temperature of 35° C. to 45° C. to get a clear solution, and then the solution was distilled under reduced pressure at a controlled temperature of 35° C. to 45° C. to a residual weight of 21.0 g to obtain an oil. 100 ml of n-heptane was added dropwise to the reaction flask. After the addition was completed, the mixture was kept at 10° C. to 20° C. for 2 hours. After the heat preservation was completed, the mixture was cooled down to 0° C. and filtered. The filter cake was dried under vacuum at 20° C., and 19.2 g of canagliflozin amorphous form was obtained as a white powdery solid with a yield of 96.0%. The ethyl acetate recovered by distillation and the n-heptane in the mother liquor can be directly used after simple water removal.

Figure 1:
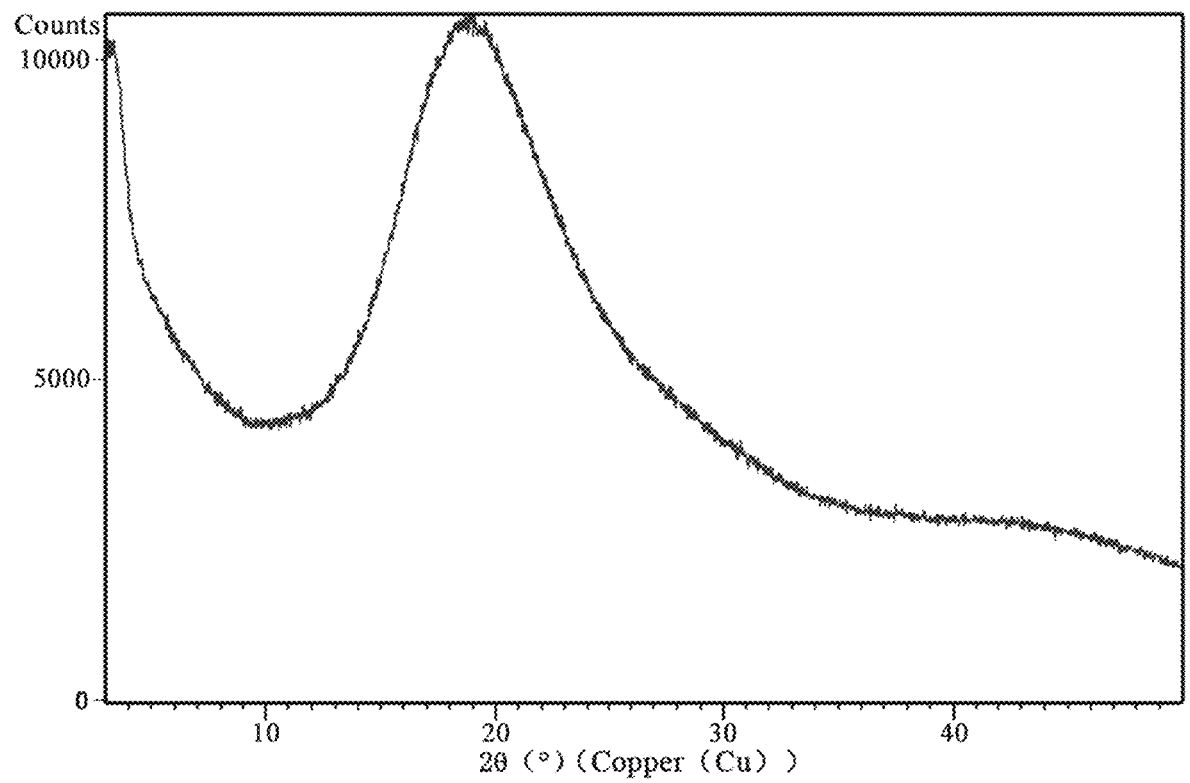
FIG. 1 is an X-ray powder diffraction pattern of the canagliflozin amorphous form prepared in Example 1 of the present invention.

FIG. 1 is an X-ray powder diffraction pattern of the canagliflozin amorphous form obtained according to Example 1. As can be seen from FIG. 1, the diffraction pattern shows that it is a typical amorphous substance.

Figure 2:
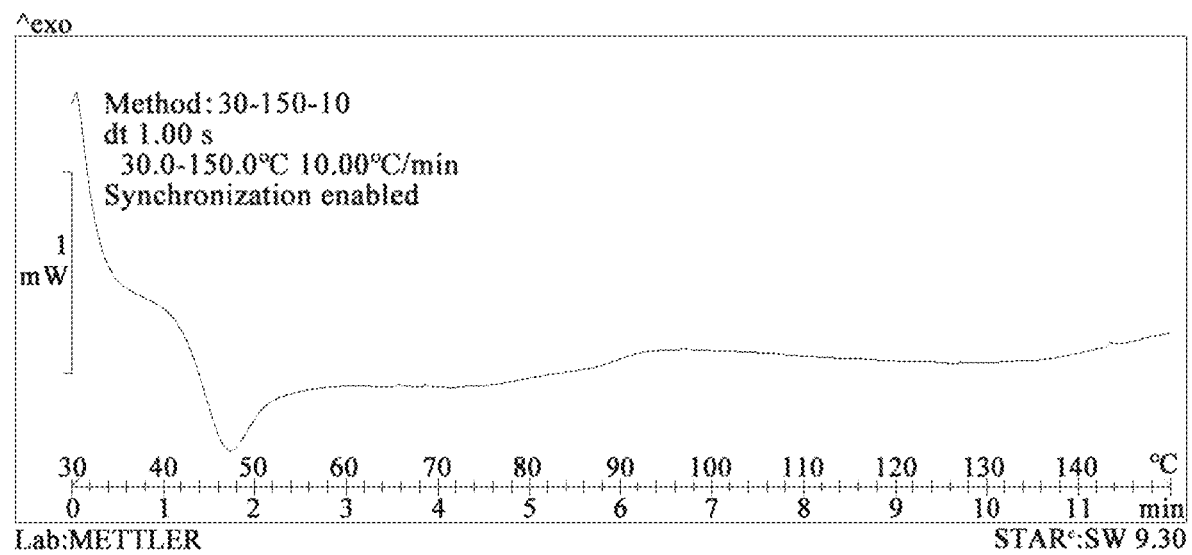
FIG. 2 is a differential scanning calorimetry diagram of the canagliflozin amorphous form prepared in Example 1 of the present invention.

FIG. 2 is a DSC spectrum of the canagliflozin amorphous form obtained according to Example 1. As can be seen from FIG. 2, there is an endothermic peak at 47° C.

Figure 3:
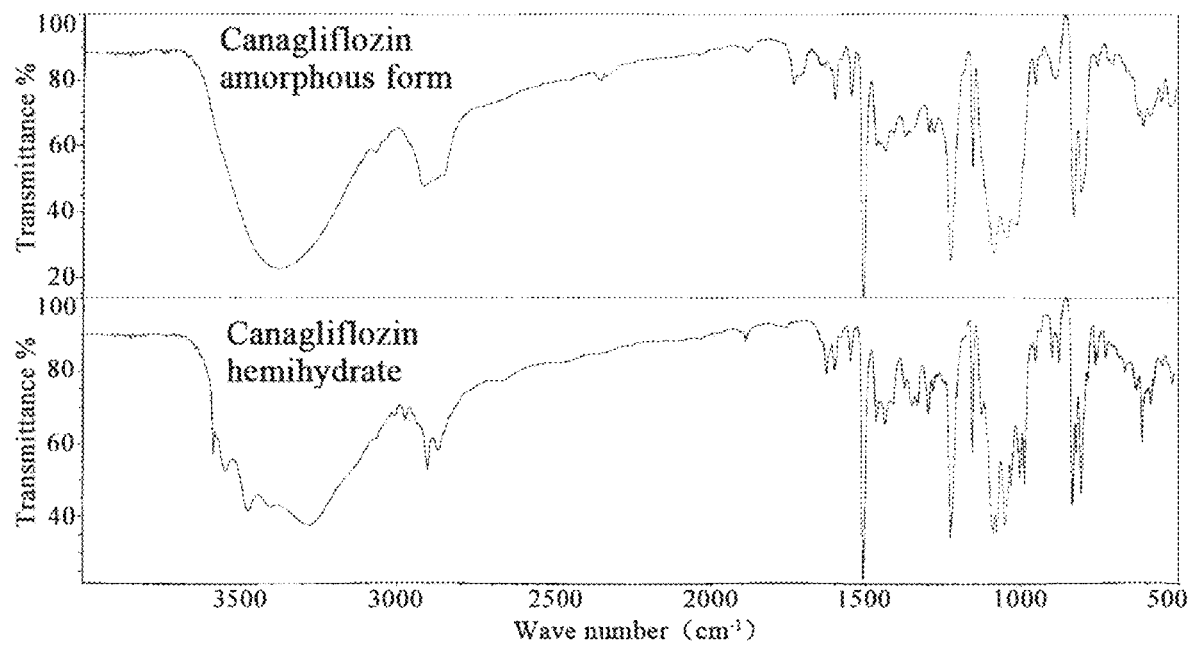
FIG. 3 is a comparison of infrared spectra of the canagliflozin amorphous form prepared in Example 1 of the present invention.

FIG. 3 is a comparison diagram of the infrared spectrum between the canagliflozin amorphous form prepared according to Example 1 of the present invention and the canagliflozin hemihydrate disclosed in Chinese Patent No.

CN101573368A. A significant difference in the characteristic peaks between the two can be seen from FIG. 3.

Figure 4:
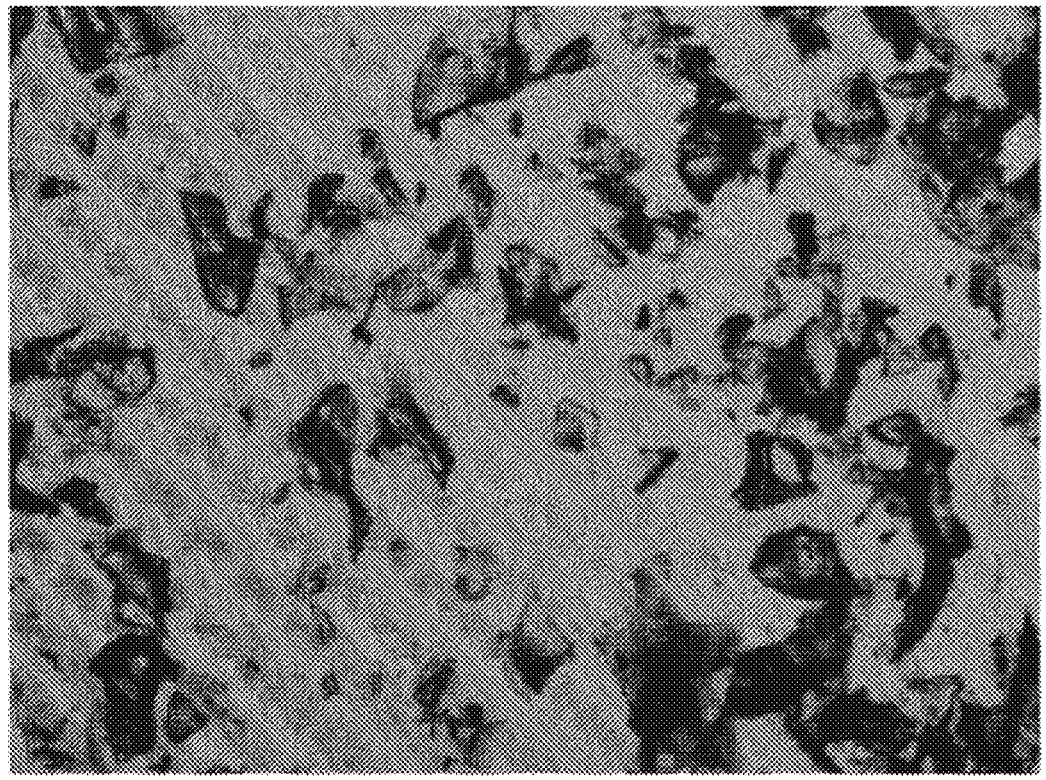
FIG. 4 is a polarizing microscope photo of the canagliflozin amorphous form prepared in Example 1 of the present invention.

FIG. 4 is a polarizing microscope photo of a canagliflozin amorphous form prepared according to Example 1 of the present invention, from which it can be seen that the product is amorphous.

Example 2

20 g of canagliflozin and 20 ml of ethyl acetate were added to the reaction flask. The mixture was stirred at a temperature of 60° C. to 70° C. to get a clear solution, and then the solution was distilled under reduced pressure at a controlled temperature of 75° C. to 85° C. to a residual weight of 21.2 g to obtain an oil. 80 ml of cyclohexane was added dropwise to the reaction flask. After the addition was completed, the mixture was kept at 20° C. to 30° C. for 2 hours. After the heat preservation was completed, the mixture was cooled to 5° C. and filtered. The filter cake was dried under vacuum at 30° C., and 19.1 g of canagliflozin amorphous form was obtained as a white powdery solid with a yield of 95.5%.

Example 3

20 g of canagliflozin and 20 ml of ethanol were added to the reaction flask. The mixture was stirred at a temperature of 65° C. to 70° C. to get a clear solution, and then the solution was distilled under reduced pressure at a controlled temperature of 45° C. to 55° C. to a residual weight of 22.0 g to obtain an oil. 60 ml of cyclohexane was added dropwise to the reaction flask. After the addition was completed, the mixture was kept at 15° C. to 25° C. for 2 hours. After the heat preservation was completed, the mixture was cooled to 10° C. and filtered. The filter cake was dried under vacuum at 30° C., and 19.4 g of canagliflozin amorphous form was obtained as a white powdery solid with a yield of 97.0%.

Example 4

20 g of canagliflozin and 30 ml of methyl tert-butyl ether were added to the reaction flask. The mixture was stirred at a temperature of 30° C. to 40° C. to get a clear solution, and then the solution was distilled under reduced pressure at a controlled temperature of 50° C. to 60° C. to a residual weight of 21.7 g to obtain an oil. 80 ml of n-hexane was added dropwise to the reaction flask. After the addition was completed, the mixture was kept at 20° C. to 30° C. for 3 hours. After the heat preservation was completed, the mixture was cooled to 0° C. and filtered. The filter cake was dried under vacuum at 25° C., and 19.2 g of canagliflozin amorphous form was obtained as a white powdery solid with a yield of 96.0%.

Example 5

The difference between Example 5 and Example 4 was that toluene was used as the organic solvent in a volume of 10 ml; n-hexane was used in an amount of 20 ml; and the yield was 95.6%.

Example 6

The difference between Example 6 and Example 4 was that tetrahydrofuran was used as the organic solvent in a volume of 100 ml; n-hexane was used in an amount of 120 ml; and the yield was 95.7%.

Example 7

The difference between Example 7 and Example 4 was that dichloromethane was used as the organic solvent in a volume of 400 ml; n-hexane was used in an amount of 400 ml; and the yield was 96.0%.

Example 8

The difference between Example 8 and Example 7 was that the mass of the oil obtained by distillation was 26 g, and the yield was 95.40%.

In order to illustrate that the canagliflozin amorphous form of the present invention is different from the amorphous form prepared by the general amorphous preparation method, the inventors select and compare the amorphous forms obtained by the above-mentioned practical methods, including rapid evaporation of solvent for curing, mixed solvent method and other related methods. The results are shown as follows:

| Preparation method of amorphous form | Product form | Stability test conditions | Obvious moisture absorption or not | Crystal transition or not | Yield |
|---|---|---|---|---|---|
| Method in the present invention Example 1 | White solid powder, good fluidity | Temperature 25 ± 5° C. Humidity 50-60%, 3 months | No obvious moisture absorption | No crystal transition | 96.0% |
| Method in the present invention Example 2 | White solid powder, good fluidity | Temperature 25 ± 5° C. Humidity 50-60%, 3 months | No obvious moisture absorption | No crystal transition | 95.5% |
| Method in the present invention Example 3 | White solid powder, good fluidity | Temperature 25 ± 5° C. Humidity 50-60%, 3 months | No obvious moisture absorption | No crystal transition | 97.0% |
| Method in the present invention Example 4 | White solid powder, good fluidity | Temperature 25 ± 5° C. Humidity 50-60%, 3 | No obvious moisture absorption | No crystal transition | 96.0% |

Figure 5:
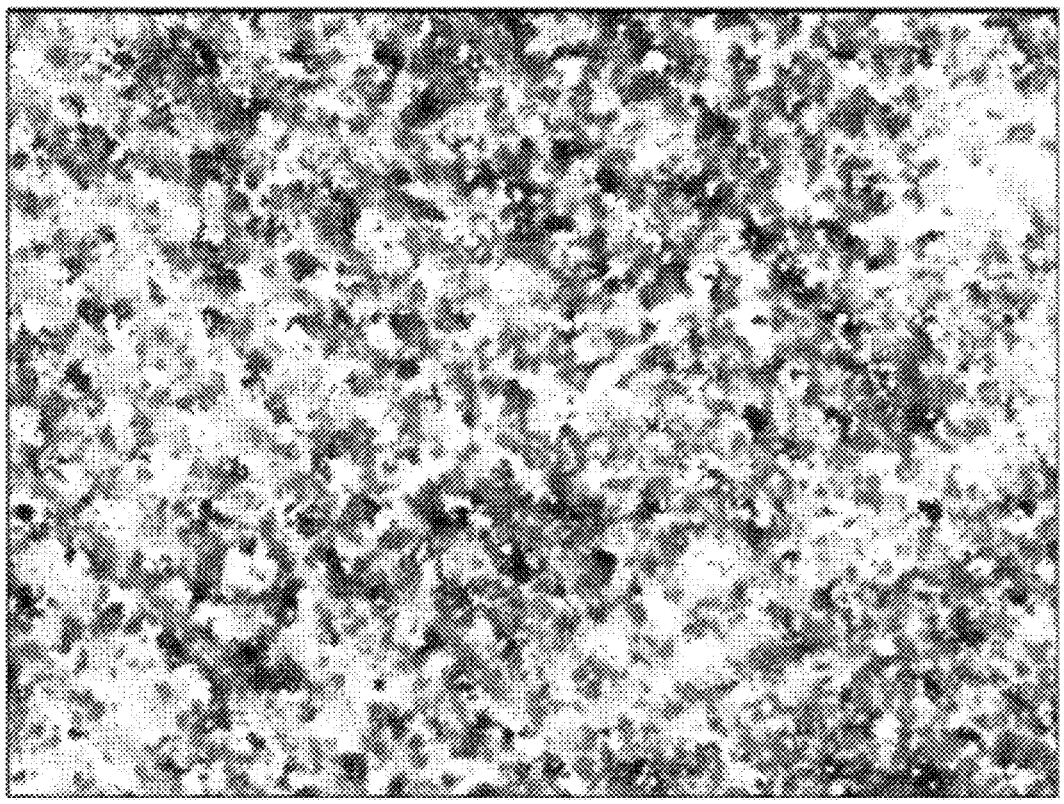
FIG. 5 is a polarizing microscope photo of the canagliflozin amorphous form obtained by a mixed solvent method according to Example 1 of CN104119323.

| Preparation method of amorphous form | Product form | Stability test conditions | Obvious moisture absorption or not | Crystal transition or not | Yield |
|---|---|---|---|---|---|
| Rapid evaporation of solvent for curing in WO2014195966 Example 3 | Yellow blocky irregular solid, poor fluidity | Temperature 25 ± 5° C. Humidity 50-60%, 3 months | Moisture absorption | Crystal transition | — |
| Mixed solvent method in CN104119323 Example 1 | White solid powder, coalesced, poor in fluidity, its polarizing microscope photo is shown in FIG. 5. | Temperature 25 ± 5° C. Humidity 50-60%, 3 months | No obvious moisture absorption | No crystal transition | 90.0% |
| Mixed solvent method in CN103889429 Example 2 | White solid powder, coalesced, high drying temperature, long time | — | No obvious moisture absorption | No crystal transition | 66.7% |
| Heat treatment method in CN105541817A Example 1 | Blocky, need to be pulverized to get the product to be applied | — | No obvious moisture absorption | No crystal transition | 99% |

"—" indicates that the item is not documented in the literature.

The above test results show that the stability of the canagliflozin amorphous form of the present invention is obviously better than that of the amorphous form prepared by rapid evaporation of solvent for curing. The yield of the canagliflozin amorphous form prepared by the method of the present invention is higher than that of the amorphous form prepared by the mixed solvent method. When comparing FIG. 5 with FIG. 4, it can be seen that the amorphous form obtained by the method of the present invention is significantly different from the amorphous form obtained by the mixed solvent method, and the product particles obtained by the present invention are larger with better fluidity. Thus, it can be seen that the form of the product obtained by the method of the present invention has obvious advantages in the process of packaging, drying, etc., compared with that of the mixed solvent method. Although the product obtained in Example 1 of CN105541817A has a high yield, but it is in the form of a block and needs to be pulverized to obtain a product to be applied, the process is more complicated.

The preparation method of the canagliflozin amorphous form disclosed in the present invention has been described by examples, and it is obvious to those skilled in the art that the method for preparing the canagliflozin amorphous form described herein can be modified or altered and combined without departing from the content, spirit and scope of the present invention to obtain the technical solutions of the present invention. It is to be understood that all such alternatives and modifications are obvious to those skilled in the art and are considered to be included in the spirit, scope and content of the invention.

The invention claimed is:

1. A method for preparing a canagliflozin amorphous form, comprising:
adding canagliflozin to an organic solvent to dissolve, distilling to obtain an oil; adding an anti-solvent to the oil, stirring to precipitate a solid, cooling, filtering, and drying to obtain a canagliflozin amorphous form, wherein a mass of the oil is 1.05-1.1 times of a mass of canagliflozin.

2. The method according to claim 1, wherein the X-ray powder diffraction pattern of the canagliflozin amorphous form shows no crystallization peak, but only a diffuse scattering peak at 10° to 30°; DSC scan of the canagliflozin amorphous form shows an endothermic peak at 40° C. to 50° C.

3. The method according to claim 1, wherein the organic solvent is selected from the group consisting of ethyl acetate, toluene, ethanol, methanol, acetone, dichloromethane, and tetrahydrofuran, or any combination thereof.

4. The method according to claim 1, wherein a ratio of a mass of canagliflozin to a volume of the organic solvent is 1 g: (0.5-20) ml.

5. The method according to claim 1, wherein dissolving is performed at a temperature of −10° C. to 120° C.

6. The method according to claim 1, wherein the anti-solvent is selected from the group consisting of n-hexane, cyclohexane and n-heptane, or any combination thereof.

7. The method according to claim 1, wherein a ratio of a mass of canagliflozin to a volume of the anti-solvent is 1 g: (1-20) ml.

8. The method according to claim 1, wherein adding the anti-solvent or stirring is performed at a temperature of 0° C. to 50° C.; the solid is cooled to −20° C. to 20° C.; drying is performed at a temperature of 10° C. to 40° C.

9. The method according to claim 1, comprising:
adding canagliflozin to an organic solvent, heating to 30° C. to 80° C. to dissolve; after dissolving, distilling a canagliflozin solution at 30° C. to 80° C. to obtain an oil, controlling a mass of the oil to be 1.05 to 1.1 times of a mass of canagliflozin, adding an anti-solvent to the oil, stirring to precipitate a solid at 10° C. to 30° C., cooling to −10° C. to 10° C., filtering, and drying at 20° C. to 30° C. to obtain a canagliflozin amorphous form.

10. The method according to claim 1, wherein the X-ray powder diffraction pattern of the canagliflozin amorphous form is shown as FIG. 1.

11. The method according to claim 1, wherein the organic solvent is selected from the group consisting of ethyl acetate, ethanol and methyl tert-butyl ether, or any combination thereof.

12. The method according to claim 4, wherein the ratio of a mass of canagliflozin to a volume of the organic solvent is 1 g: (1-5) ml.

13. The method according to claim 5, wherein dissolving is performed at a temperature of 30° C. to 80° C.

14. The method according to claim 1, wherein the anti-solvent is cyclohexane or n-heptane.

15. The method according to claim 7, wherein the ratio of a mass of canagliflozin to a volume of the anti-solvent is 1 g: (3-6) ml.

16. The method according to claim 8, wherein adding the anti-solvent or stirring is performed at a temperature of 10° C. to 30° C.

17. The method according to claim 8, wherein the solid is cooled to −10° C. to 10° C.

18. The method according to claim 8, wherein drying is performed at a temperature of 20° C. to 30° C.

* * * * *